United States Patent [19]

Wijangco et al.

[11] Patent Number: 4,863,582

[45] Date of Patent: Sep. 5, 1989

[54] PROCESS AND APPARATUS FOR PURIFYING AND CONCENTRATING DNA FROM CRUDE MIXTURES CONTAINING DNA

[75] Inventors: Antonio Wijangco, South Salem; Theresa Guarino, Fishkill; Robert Zahensky, Yorktown Heights, all of N.Y.

[73] Assignee: Lifecodes Corporation, Valhalla, N.Y.

[21] Appl. No.: 173,159

[22] Filed: Mar. 28, 1988

[51] Int. Cl.$^4$ .................. G01N 27/28; G01N 27/26
[52] U.S. Cl. .................. 204/299 R; 204/182.8; 204/301
[58] Field of Search ........... 204/301, 299 R, 182.8, 204/182.9, 182.3, 180.1

[56] References Cited

U.S. PATENT DOCUMENTS

4,617,102 11/1986 Tomblin et al. ............. 204/301 X

Primary Examiner—John F. Niebling
Assistant Examiner—John S. Starsiak, Jr.
Attorney, Agent, or Firm—John F. Ohlandt

[57] ABSTRACT

In an apparatus for purifying and concentrating DNA, from a crude mixture containing DNA, a unitary collection cup for collecting the DNA from a lysate sample is provided; also, a retainer member for retaining a gel matrix. Both the collection cup and the gel matrix, which is disposed above the collection cup, are adapted to be engaged with a lysate container. The container functions to receive the lysate sample, which sample typically is derived from human whole blood; rotation of the lysate sample container produces opening and closing of a pathway defined by slotted passages in the collection cup, thereby selectively controlling the flow of electrophoresis buffer solution through the interior of the collection cup at appropriate times.

18 Claims, 6 Drawing Sheets

PROCESS AND APPARATUS FOR PURIFYING AND CONCENTRATING DNA FROM CRUDE MIXTURES CONTAINING DNA

BACKGROUND OF THE INVENTION

The present invention relates to the field of extraction of high molecular weight DNA from test samples, particularly from human whole blood samples.

The present invention is an improvement on the apparatus and process previously described and claimed in a related application, Ser. No. 714,376, now U.S. Pat. No. 4,617,102, assigned to the assignee of the present application. In that related application, the basic process and apparatus are directed to the collection of DNA of usable volume and concentration and of such purity as to permit conventional restriction by a number of enzymes without the need for further purification. Essentially, the apparatus described in the related application consists of an agarose gel disk, typically 5 millimeters thick by 31 millimeters in diameter, which is immersed in an electrophoresis buffer solution and supported between 8 micrometer polycarbonate filters in an electric field.

Considered in some detail, the process of the related U.S. Pat. No. 4,617,102 involves the loading of a suitably treated sample, such as blood lysate, onto the top face of the agarose gel disk and then applying the electric field. It turns out that of the total constituent parts of the treated blood, the DNA molecules are by far the largest in respect to molecular weight. Consequently, their passage through the agarose gel disk, under the force of the electric field, is impeded such that the time period governing their removal is substantial. All other constituent parts of the treated blood pass relatively rapidly through the gel disk and are readily removed, being swept away by flow of the buffer solution. The DNA is then eluted and collected in concentrated form by application of the electric field, while the normal flow of buffer solution between the bottom of the gel matrix and a collection chamber is prevented. Other and further details of the constuction of the DNA extraction apparatus may be appreciated from the cited related application, such details being incorporated herein by reference where appropriate.

Although the process and apparatus described in the related application, and briefly summarized above, have functioned to provide DNA of usable volume and concentration, it turns out to be highly desirable to be able to operate even more efficiently in the processing of a blood lysate sample for removal of DNA, particularly to be able simply and quickly to remove a given collection cup, in which the DNA has been recovered, from the machine or apparatus, and to replace it immediately with an identical collection cup. The DNA captured on the membrane in the given collection cup is then removed for further processing. The gel matrix retainer member associated with the collection cup is normally the only disposable unit; however, the entire assembly could be made disposable. As a consequence of this replaceable construction, the processing operation can be made substantially continuous.

Accordingly, it is a primary object of the present invention to further reduce the processing times involved in the operation of extracting the DNA from test samples.

Another object is to provide a more efficient way of removing all of the unwanted constituents from the blood lysate or other sample when that part of the procedure is being carried out and, likewise, to readily remove from the machine or apparatus the collection cup in which the DNA has been collected; furthermore, to be able easily and quickly to separate the individual parts of the collection cup when so removed, thereby to have access to the collected DNA.

Another object is to provide a simpler mechanism—and one that permits more relaxed tolerances on parts—for collecting the laminar flow of buffer solution at the different stages in the operation of the DNA extraction process.

SUMMARY OF THE INVENTION

The above and other objects are fulfilled and implemented by the several features of the present invention. Briefly described, the present invention is operative in the basic context already described in related U.S. Pat. No. 4,617,102. The process disclosed in that related application includes the steps of first preparing a test sample, and as a specific example, a whole blood lysate sample; followed by the step of placing the sample in apparatus developed in accordance with the invention described in that related application, whereby a series of operations are performed that yield a usable and convenient quantity of DNA.

A primary feature of the present invention, which represents an improvement over that of the related application already noted, resides in a more efficient way of controlling the removal of all of the unwanted constituents from the blood lysate, or other sample and collecting the DNA. This feature enables very simple manipulation, involving rotation, of the sample-holding container—which will be referred to hereinafter as the lysate container - to effectuate the DNA collection. As a consequence, one can switch from permitting laminar flow of buffer solution, thereby sweeping away unwanted constituents, to blocking such flow. A retainer member, in which the gel matrix is held, fits inside the lysate container and engages at an opening in a suitably located wall of the container, such that the sample can be drawn into the gel matrix.

In operation, a quantity of electrophoresis buffer solution is held in a tank which includes, as an integral part, a cylindrical vessel. The vessel normally becomes filled with the buffer solution. The lysate container is formed to be fitted inside the vessel and hence to be immersed in the buffer solution. Since it is provided with suitable openings, the interior of the lysate container becomes filled with buffer solution.

In a preferred embodiment, as will be made clear hereinafter, the collection cup comprises two interfitting parts: a lower part provided with a conical recess, and an upper part having (1) a collection chamber with slotted passageways and (2) a conical lower portion for tightly engaging with the lower part. The engagement of these two parts functions to hold a dialysis membrane over a central opening formed in the parts such that the DNA which is eluted from the gel matrix into the collection cup can be captured on the membrane. Alternatively, the entire collection cup could be formed as one piece by a suitable molding process, and thereby could be selectively disposable as an entire unit. To this end, the dialysis membrane could be placed within the mold as the plastic material constituting the collection cup is being molded. Consequently, the membrane would become suitably embedded and would extend over the desired opening, which would also be created in the molding process.

Other and further objects, advantages and features of the present invention will be understood by reference to the following specification in conjunction with the annexed drawing, wherein like parts have been given like numbers.

DESCRIPTION OF PREFERRED EMBODIMENT

Before proceeding with a detailed description of the preferred embodiment, it should be recalled that the present invention is an improvement on that disclosed in related application 714,376 filed March 21, 1985, now U.S. Pat. No. 4,617,102. The fundamental principles which were described in the related patent are applicable to the present invention. In particular, the concept or principle of completely separating the unwanted constituents from a crude mixture which contains DNA such that the pure concentrated DNA can be extracted is known from that related application. Also, the discovery that significantly different time periods govern the removal by electrophoretic action of the unwanted constituents and the wanted DNA, is likewise herein exploited. However, as noted previously herein, greater efficiency is enabled as will be made clear hereinafter by the particular construction of the apparatus herein and by the improved associated technique which has been developed in accordance with the present invention.

It should be particularly noted that the requirements on tolerances involved in manufacturing the different parts in accordance with the present invention is greatly relaxed from those involved in the invention of the related application.

Referring now to the figures of the drawing, that is, to FIGS. 1–10, there will be seen an extraction apparatus or assembly 10 comprising a tank 12 for containing a reservoir 14 of electrophoresis buffer solution. Forming an integral part of tank 12 is a cylindrical vessel 16 having a platform 18 at its upper end.

Figure 1:
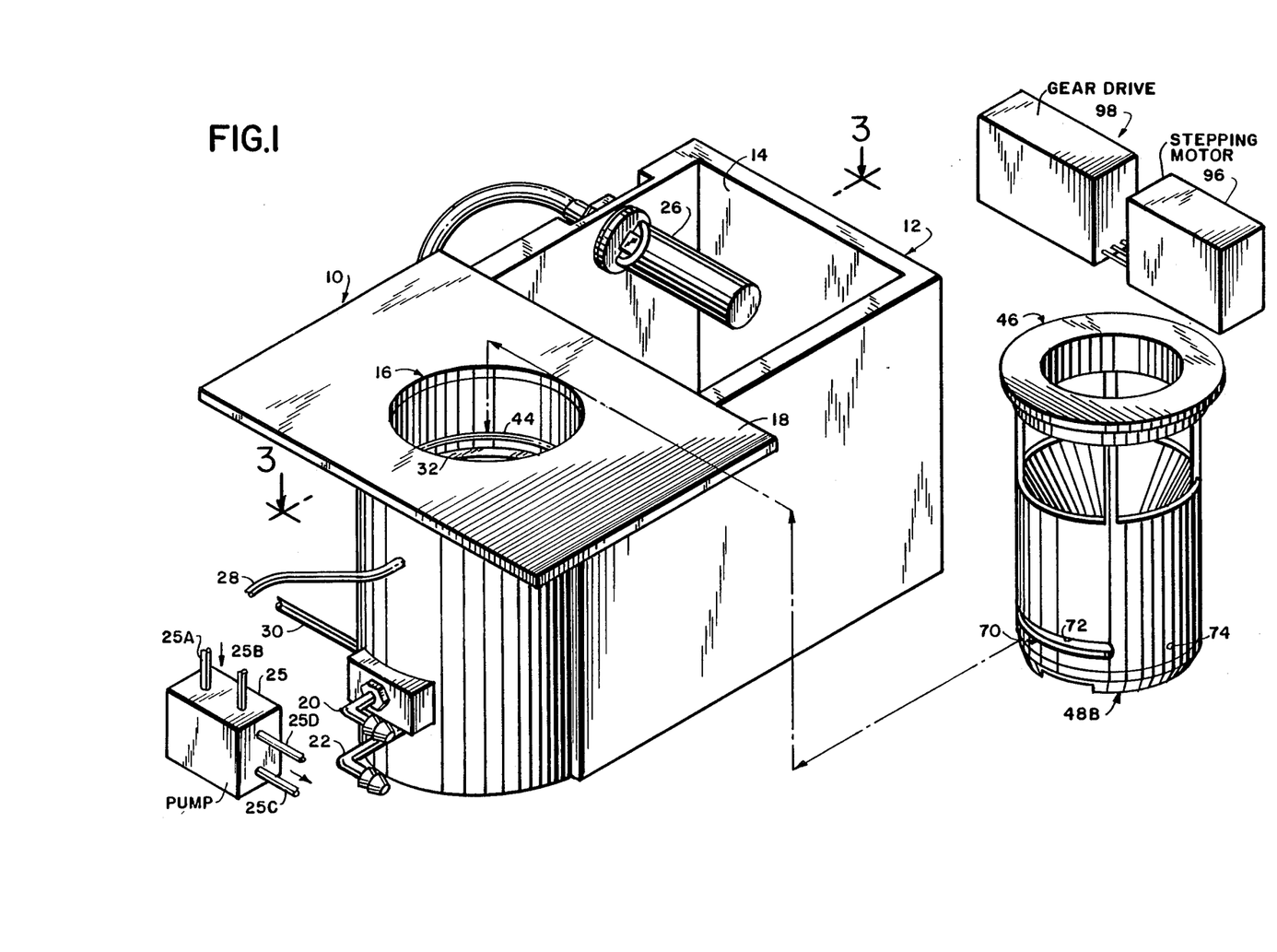
FIG. 1 is an exploded perspective view of the apparatus in accordance with the preferred embodiment of the present invention, illustrating the lysate container removed from the tank holding the reservoir of electrophoresis buffer solution.
Figure 2:
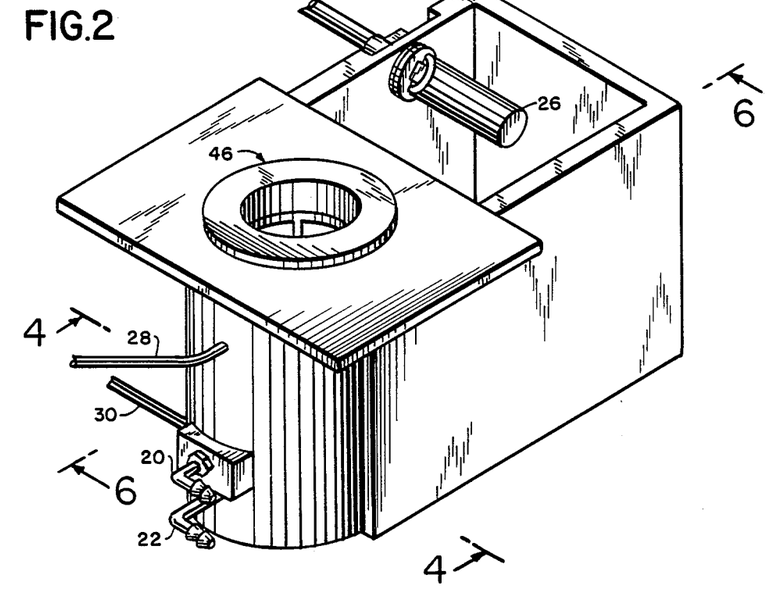
FIG. 2 is another perspective view of the apparatus showing the lysate container fitted into the cylindrical vessel forming part of the tank.

Two separate inlets 20 and 22 are seen at the bottom of the cylindrical vessel 16, at the near end as seen in FIG. 2, for permitting fluid flow from a suitable source in separate pathways into the cylindrical vessel 16, and thence, by openings 23A and 23B, into the reservoir 14. Opening 23B enables the flushing away of any bubbles formed at the electrode 42. Another inlet 24 to the tank is seen at the far end in FIG. 2. Its purpose is to fill the tank at the beginning of a given run. To enable proper recirculation of the electrophoresis buffer solution which is to be utilized in the technique of the present invention, a means such as the pump 25 is utilized. A suitable outlet connection 27 for this purpose is provided at the bottom of tank 12 (FIG. 3).

Separate input connections 25A and 25B to the pump, as well as output connections 25C and 25D, are provided to permit appropriate recirculation and to drain the apparatus of solution.

For fluid level sensing purposes, a level sensor device 26 is disposed within the tank 12 and is immersed in the buffer solution. It will also be noted that suitable electrical leads 28 and 30 serve to connect a source of power, not seen, to spaced electrodes to be described.

Figure 3:
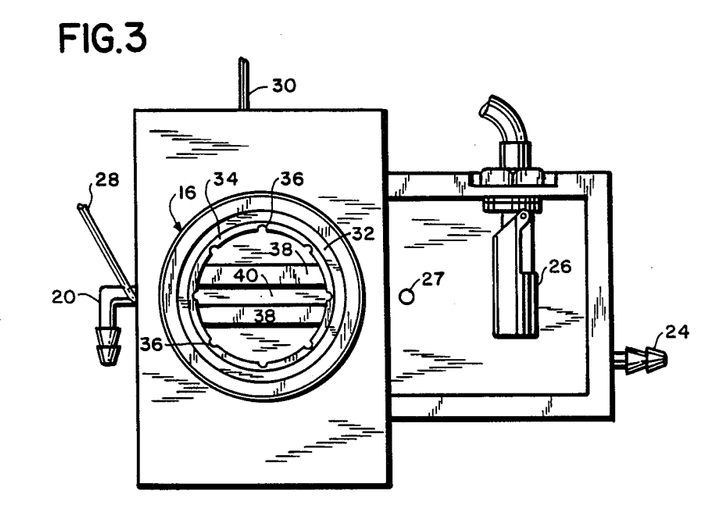
FIG. 3 is a top plan view of the apparatus, especially illustrating the interior of the cylindrical vessel.

Referring now to FIG. 3, the interior of the vessel 16 may be seen in more detail. At the upper portion, an annular guide flange 32 is provided. Further down within the cylindrical vessel 16 is an additional annular guide flange 34, suitably provided with openings 36 to enable the buffer solution to fill the cylindrical vessel.

At the bottom of the vessel 16 (FIG. 3) are a pair of bosses or rails 38 which are suitably spaced to form a trough or passageway 40 for the transverse flow of fluid in the vessel from the inlet 22 to the opening 23B therein. It will be seen that a positive electrode 42 extends upwardly into the trough. The negative electrode 44 (FIG. 1) which together with electrode 42 provides the necessary electric field, is in the form of a ring and is situated above the upper annular flange 32.

Figure 7:
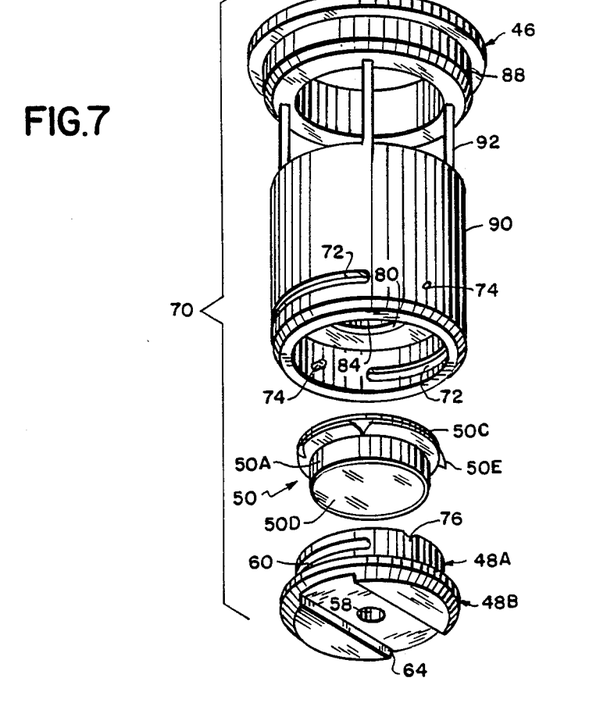
FIG. 7 is an exploded view of the lysate container and of the parts that fit within the lower portion of such container, that is, the retainer member for the gel matrix and the collection cup.
Figure 8:
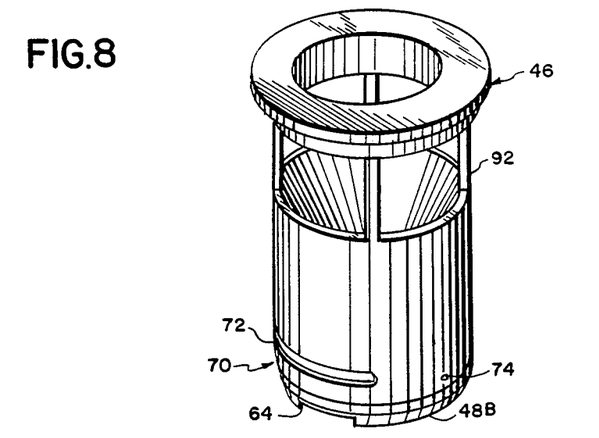
FIG. 8 is another perspective view of the lysate container.
Figure 9:
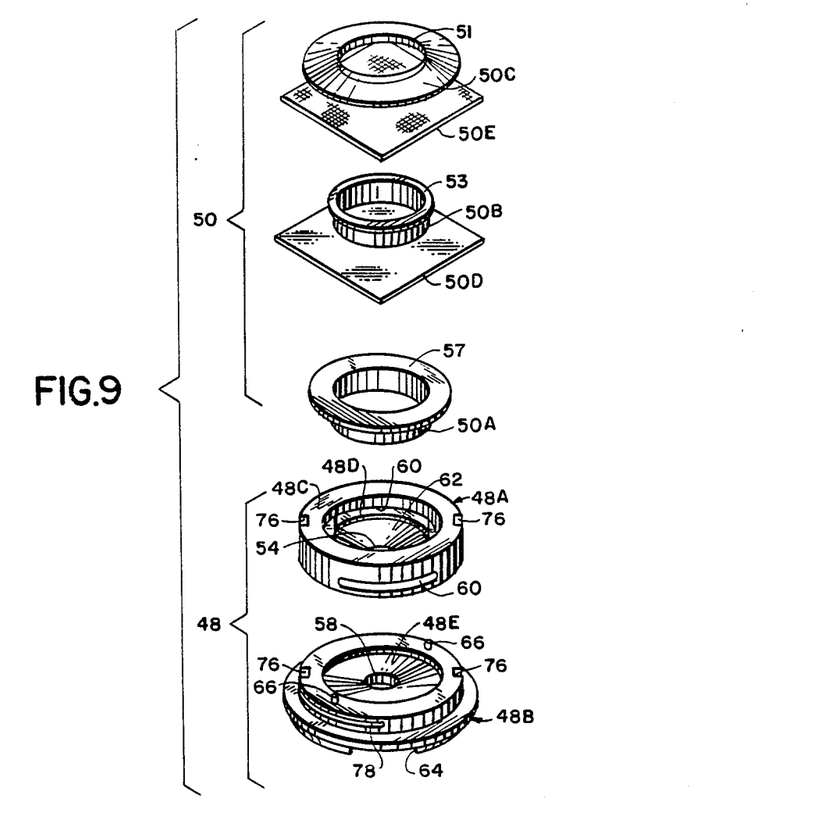
FIG. 9 is an exploded view of all of the elements of the retainer member, and also of the elements constituting the collection cup.
Figure 10:
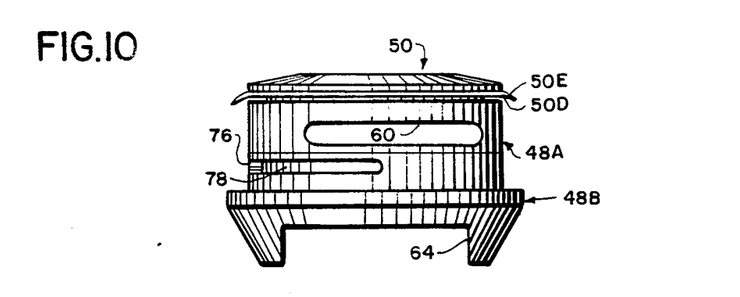
FIG. 10 is an elevational view of all of the parts or elements shown in FIG. 9, but brought together in interfitting operative fashion.

Referring now to FIGS. 4–10, there will be appreciated from these views the construction of a lysate container 46, and, adapted to be engaged with such container, a collection cup 48 and a gel matrix retainer 50 (FIG. 7). The collection cup 48 includes an upper part 48A and a lower part 48B (FIG. 9). The lower part 48B can be seen in FIG. 8 extending from the lower end of the assembled lysate container 46.

Seen in detail in FIG. 9 is the gel matrix retainer member 50 comprising five separate elements in this particular embodiment. These elements are rings or hoops 50A, 50B and 50C; and nylon mesh, or polycarbonate membrane, elements 50D and 50E. The latter two elements contain a suitable agarose gel matrix between them, the gel being of the type disclosed in related U.S. Pat. No. 4,617,102.

Figure 4:
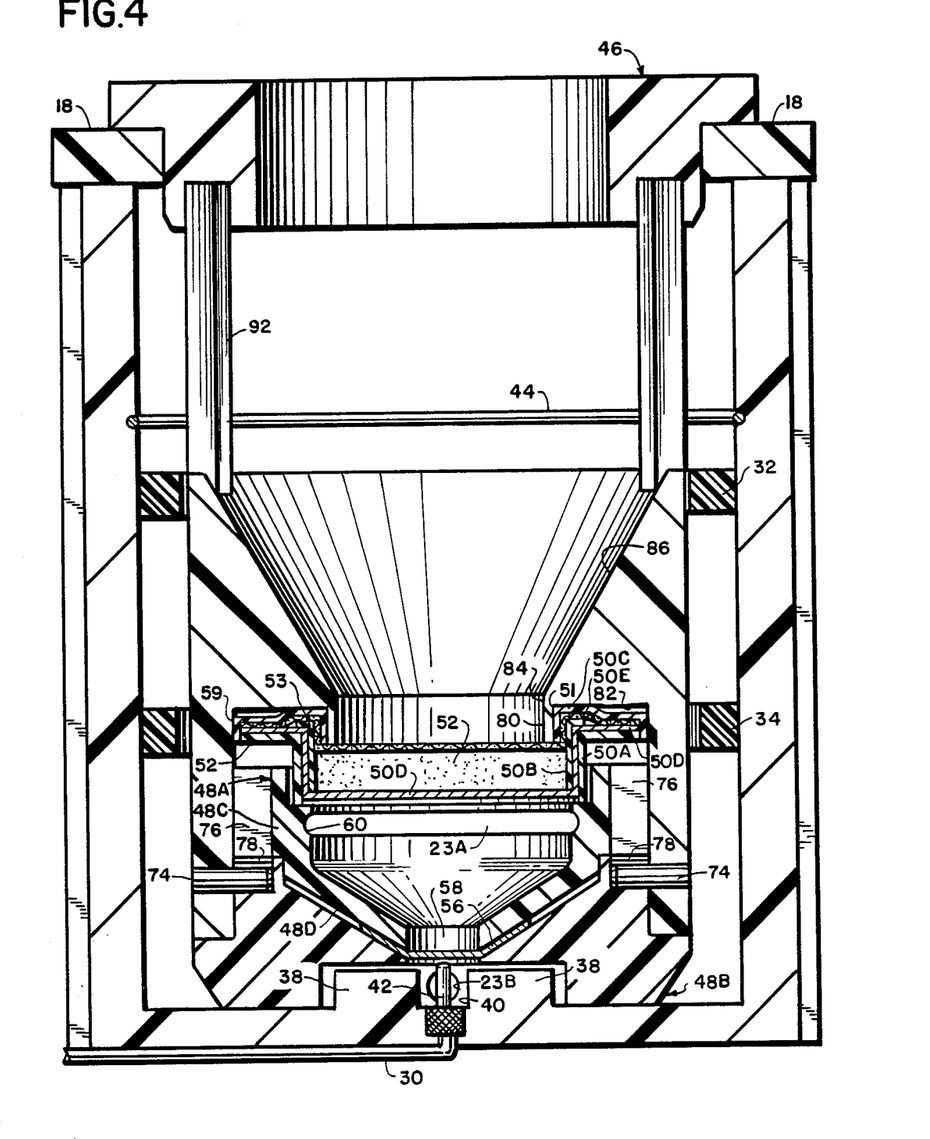
FIG. 4 is a vertical sectional view taken through the apparatus, along the line 4—4 in FIG. 2, illustrating the situation where the lysate container is in its operative position in the vessel of the apparatus and, in particular, showing the open state for the valve means of the apparatus.
Figure 5:
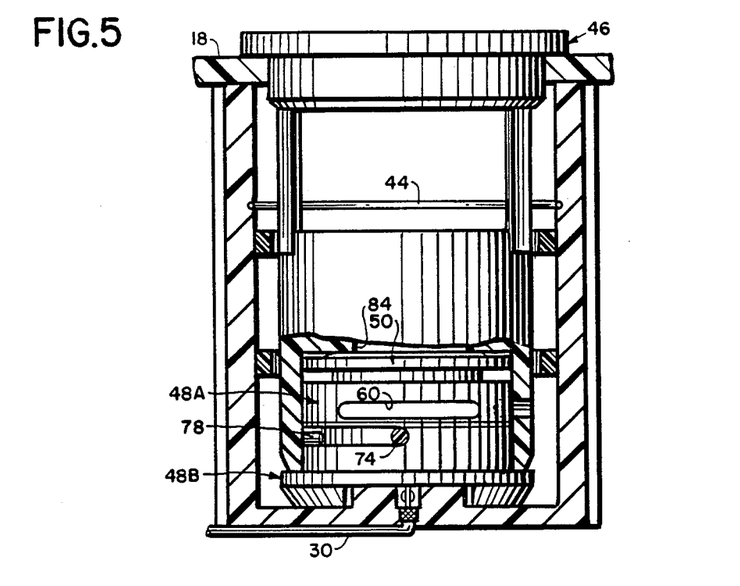
FIG. 5 is an elevation view, partly broken away to illustrate the collection cup, the valve means at this point being in the closed state.
Figure 6:
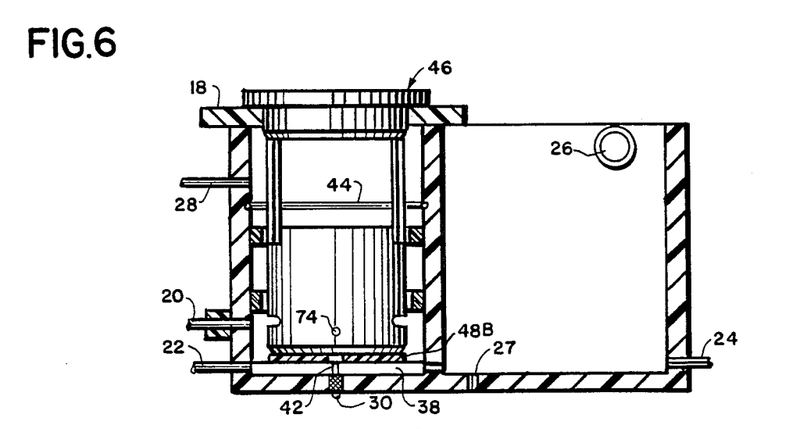
FIG. 6 is a longitudinal sectional view taken on the line 6—6 of FIG. 2.

Also seen in FIG. 9, as well as in FIGS. 4, 5 and 7, is the particular construction for the collection cup 48. This collection cup is basically constructed, in the particular embodiment shown, of the two parts 48A and 48B, the upper part having a generally annular upper portion 48C with a thin-walled conical lower portion 48D, the latter including an opening 54 at its apex (FIG. 9).

The lower part 48B of the collection cup has a dish-shaped or conical portion 48E integrally formed with an annular portion 48F. Portion 48E is adapted to receive and fill closely with the conical portion 48D of the upper part; moreover, tightly engaged therebetween is a dialysis membrane 56 (FIG. 4) for the purpose of capturing the DNA which is eluted from the gel plug or matrix 52. To this end, the dish-shaped portion 48E includes an opening 58 which aligns with the corresponding opening 54 in the upper part.

Of special interest in the construction of the annular portion 48C are the two slotted passages 60 therein, which are diametrically opposed and are adapted for the purpose of permitting flow of buffer solution into and out of the chamber 62 defined at the interior of the upper part 48A of the collection cup 48. It is these slotted passages that are selectively opened or closed by rotation of the lysate container, as will be explained in some detail hereinafter. These passages 60 are opened to permit the sweeping away of the undesired constituents of the lysate sample at one stage of the process. At another stage, i.e., when the DNA is to be eluted and collected, they are closed to block the flow of the buffer solution, thereby to avoid sweeping away the DNA.

Lower part 48B of the collection cup is provided with a groove 64 of sufficient width to straddle the bosses or rails 38 which define the trough 40 in the vessel 16 (FIG. 3). As a consequence, the lower part 48B is fixed against rotation about its axis, which corresponds with the axis of lysate container 46. Also, because of the provision of pins 66, which are received into holes (not seen) formed at the lower surface of upper part 48A of the collection cup, such part also becomes fixed against rotation when abutted against lower part 48B.

In order that proper selective operation may be effectuated, a valve means 70 is provided; such valve means is partly defined or formed by the aforenoted slotted passages 60 in the collection cup, and by a pair of corresponding slotted passages 72 in the lysate container 46 (FIGS. 7 and 8).

It should also be noted in this connection that a pair of pins 74 are also provided at the interior of container 46, extending through such that they are seen at the exterior in FIGS. 7 and 8. These pins are received in cooperating grooves in the parts 48A and 48B of the collection cup. Thus, a pair of axially extending grooves 76, located at the periphery in the upper part 48A, align with the axially extending portions at the ends of circumferentially extending grooves 78 in the lower part 48B.

It will be understood that when the DNA extraction process is to be carried out, the lysate container 46, as seen in the exploded view of FIG. 7, is inverted from the position shown therein and the gel matrix retainer 50 is initially inserted into the bottom portion of the container 46 such that the periphery 51 of hoop 50C surrounds a ring 80 depending from a shoulder 82 in the container 46. As a result, the mesh or screwn 50E abuts against the bottom of ring 80 and extends over an opening 84 defined thereby (FIG. 4), being retained by the engagement of a flange 53 on hoop 50B (FIG. 9) with an inner groove 55 formed at the underside of hoop 50C. It will be seen that the opening 84 is disposed at the bottom of a conical section 86 formed at the interior of container 46.

It will also be seen that the lower mesh or screen 50D defines the bottom of the retainer member 50, being stretched across the bottom by reason of engagement between the peripheries of the hoops 50A and 50B. It will be noted that hoop 50A includes a flange 57 adapted to be received in an outer groove 59 in hoop 50C.

Subsequently to placing the retainer member 50 into the lysate container 46 as just described, the collection cup 48 is engaged with the bottom of this container. The collection cup is positioned such that its diametrically opposed pairs of axially and circumferentially extending grooves 76 and 78 in the respective parts 48A and 48B, are brought into alignment with the pins 74 at the bottom of container 46. The collection cup is then rotated appropriately, that is, to an extent sufficient to cause engagement with the container, whereby the collection cup cannot drop away from the container 46. Thereafter, the whole assembly is placed into the vessel 16 of the tank 12 so that the groove 64 overlies and spans the trough 40. Consequently, the collection cup will become fixed against rotation, and the lysate container can be rotated relative to the collection cup by manually grasping the flange or by employing a suitable mechanical means such as the stepping motor shown schematically at 96, which is coupled with suitable gear drive 98, so that the pins 74 are returned to the position at which they began, that is, to the axially extending end portions of the circumferentially extending grooves 78.

In the above-noted position for the lysate container, it will be understood that the passages 72 in the lysate container are circumferentially aligned with the corresponding slotted passages 60 in the collection cup. This is the open position for the valve means 70, as particularly illustrated in FIGS. 4 and 6.

In accordance with this position for the valve means 70, the extraction process will be operating at the stage where the contaminants are to be removed from the crude mixture containing the DNA, that is, just after the time when the lysate sample has been poured into the open top of the lysate container 46, i.e., at the gaps between the upper portion 88 of the container and the main or body portion 90. Struts 92, seen in FIG. 7, connect these parts or portions.

Accordingly, the electrophoresis buffer solution present in the tank will be drawn in a laminar flow through the slotted passages 72 in the lysate container and the slotted passages in the collection cup 36. Because of the presence of an appropriate electric field, and because of the time period that will have elapsed since drawing the lysate sample into the gel, the relatively small molecule constituents, i.e., all constituents other than the DNA that one wants to remove, will begin to pass from the gel matrix and into the chamber 62, whence they are swept away by the laminar flow that has been permitted to be generated. As a consequence, all of the undesired contaminants are removed.

However, when a sufficient time has elapsed, of the order of several hours from the point when all of the contaminants clearly have been removed, it is then desired to collect the DNA that remains in the gel matrix 52. What is first done is the electric field is increased. The lysate container is then rotated counterclockwise either manually or by the automatic means 96, to a point such that the pins 74 on the wall of the container have progressed, as seen in FIG. 5, to the end of their travel in the grooves 78. This is the closed position for the valve means 70 because the noted movement of the container about the fixed collection cup results in solid portions of the wall of the container confronting the slotted passages 60 in the collection cup. Thus, the passages 60 are effectively blocked and no flow of buffer solution is now possible into the chamber 62. As a result, the DNA which is eluted, that is, flows out of the gel matrix 62, moves downward and is captured or retained on the dialysis membrane 56 held between the upper and lower parts of the collection cup 48.

Although in a previous discussion the retainer member 50 was considered a single disposable entity, while the collection cup was replaceable but non-disposable, it will be appreciated that the entire assembly of both the gel matrix retainer member 50 and the collection cup 48 could be manufactured as a single, disposable entity.

In order to enable the man skilled in the art to practice in some detail the technique in accordance with the present invention, the following protocol is herewith provided:

The operation of the novel machine or apparatus already described consists of four cycles, (RUN, RINSE1, RINSE2, ELUTE), spanning over approximately 7 hours. The following describes how the machine operates in these four cycles.

I RUN Cycle

1. The lysate chamber is in place and in the open position. The lystate is loaded above the gel.
2. A first valve in the lines connecting to the apparatus allows RUN buffer to enter the lysate chamber. This valve remains open until the level sensor 26 detects a "full" condition.
3. The circulation pump 25 and the electric field are activated. At this time, the lysate begin to migrate into the gel.
4. After 2½ hours, the electric field is deactivated.
5. An exit valve opens, allowing buffer to exit the chamber.
6. After 1 minute, the exit valve and the circulation pump 25 are deactivated (chamber now empty).
7. The machine now enters the RINSE1 cycle.

II RINSE1 Cycle

8. A second valve opens, allowing RINSE buffer to enter the chamber. This valve remains opn until the level sensor detects a "full" condition.
9. The circulation pump and the electric field are activated. At this time, most of the heme has been removed in the RUN cycle, but the DNA continues to migrate in the gel.
10. After 40 minutes, the electric field is deactivated.
11. The exist valve opens, allowing buffer to exit.
12. After 1 minute, the exit valve is closed and the circulation pump is turned off (chamber again empty).
13. The machine now enters its third cycle.

III RINSE2 Cycle

14. The conditions in RINSE2 are identical to those of RINSE1, i.e., steps 8–12 are repeated.

The approximately 4 hours involved in the RUN cycle and the two Rinse cycles is called the "window of opportunity" because it insures that all of the small molecule contaminants will have passed out of the gel, while the DNA remains in the gel because of its much larger molecular size.

15. The machine now enters its fourth cycle.

The purpose of the second rinse cycle is to eliminate any low level "contaminant" that accompanied the DNA.

IV ELUTE Cycle

16. The second valve opens, allowing RINSE buffer to enter the chamber. This valve remains open until the level sensor detects a "full" condition.
17. The circulation pump 25 is activated.
18. The lystate chamber is rotated 90 degrees to a closed position.
19. The electric field is activated. At this time, the DNA migrates out of the gel and into the elution chamber.
20. After 3 hours, the electrode is deactivated. At this time, the DNA is attached to the dialysis membrane.
21. The exit valve opens to allow buffer to exit.
22. After 1 minute, the circulation pump and the exit valve turn off.
23. DNA is now ready for collection.

While there has been shown and described what is considered at present to be the preferred embodiment of the present invention, it will be appreciated by those skilled in the art that modifications of such embodiment may be made. It is therefore desired that the invention not be limited to this embodiment, and it is intended to cover in the appended claims all such modifications as fall within the true spirit and scope of the invention.

We claim:

1. Apparatus for purifying and concentrating DNA from a crude mixture containing DNA comprising:
    (a) a tank providing a reservoir of electrophoresis buffer solution;
    (b) means coupled to said tank for producing flow of buffer solution therethrough;
    (c) a rotatable container, disposed in said tank, for holding said crude mixture in the form of a test sample, said container having passages therethrough;
    (d) a gel matrix immersed in said buffer solution and disposed within said container;
    (e) an electric field coupled to said gel matrix;
    (f) a collection cup, having a common axis with, and engageable with the bottom of, said container, for collecting the DNA coming out of said gel matrix, said cup including a chamber at its interior and passages formed through said cup to said chamber for permitting flow of said buffer solution into said chamber from said tank when the passages in said collection cup are aligned with the corresponding passages in said rotatable container;
    (g) said rotatable container having portions for selectively closing said passages in said collection cup;
    (h) means for selectively activating said electric field for predetermined discrete time periods such that for a first period all constituent molecules of the test sample, except for the DNA, are selectively removed from said gel matrix, said constituents being swept away by said flow of said electrophoresis buffer solution because of alignment of the passages in said container with the passages in said collection cup; and for a second period, the DNA left behind during the first period is collected because the passages in said collection cup are closed.

2. Apparatus as defined in claim 1, further including a dialysis membrane on which the DNA is captured, and in which said collection cup comprises an upper and lower part, said chamber being defined at the interior of the upper part; both the upper and lower part having tightly fitting portions between which said dialysis membrane is held.

3. Apparatus as defined in claim 2, further including a pair of circumferentially extending grooves in the lower part and, adapted to meet respectively therewith, a pair of axially extending grooves in the upper part; a pair of pins affixed to said container for engagement with the respective meeting grooves of the two pairs.

4. Apparatus as defined in claim 3, in which when the rotatable container is positioned such that said pins are at the meeting point of the respective grooves, the container passages overlie the collection cup passages, whereby said pathway is completed.

5. Apparatus as defined in claim 2, in which said tightly fitting portions are conical, and aligned openings are provided in the respective portions.

6. Apparatus as defined in claim 2, in which the passages formed in the collection cup are diametrically opposed for defining a pathway for said buffer solution flow; and corresponding diametrically opposed passages are formed in said container to selectively align with the collection cup passages for completing said pathway.

7. An apparatus as defined in claim 1, in which the test sample is blood lysate.

8. Apparatus as defined in claim 1, further comprising a retainer member for retaining said gel matrix, said retainer member being adapted to be disposed above said collection cup in coupling relationship therewith.

9. Apparatus as defined in claim 1, further including a cylindrical vessel forming an integral part of said tank, said container being immersed in the buffer solution within said vessel.

10. Apparatus as defined in claim 9, further including spaced rails at the bottom of said vessel, and in which a groove is formed at the bottom of the collection cup to span said spaced rails, thereby to fix said collection cup against rotation.

11. An assembly adapted to be engaged with a test sample container for use in an apparatus for purifying and concentrating DNA, said assembly comprising:
a dialysis membrane on which the DNA is to be captured; and a collection cup including an upper and lower part, said parts having respective portions that fit closely together and tightly engage between them said dialysis membrane; said collection cup having a pair of passages extending from outside said cup to a chamber at the interior thereof;
a gel matrix; and a retainer member for retaining the gel matrix, said member including means for enabling said member to be disposed above said collection cup in coupling
relationship therewith, said retainer member comprising a plurality of hoops, the gel matrix being confined between screens held by respective pairs of hoops.

12. An assembly as defined in claim 11, further including means for selectively engaging said collection cup with the test sample container.

13. An assembly as defined in claim 12, in which said upper part includes a pair of diametrically opposed axially extending grooves, and said lower part includes a pair of circumferentially extending grooves that respectively meet with the axially extending grooves so as to define said means for selectively engaging the collection cup with the container.

14. An assembly as defined in claim 13, in which aligned openings are included in the portions of the upper and lower parts that fit closey together and tightly engage said dialysis membrane.

15. An assenbly as defined in claim 14, in which said screens are constituted of nylon mesh.

16. An assembly as defined in claim 11, in which said pair of passages in said collection cup are diametrically opposed.

17. An assembly as defined in claim 16, in which said collection cup includes an upper and a lower part, said upper part having said diametrically opposed pairs of passages therein and said lower part having a groove at its bottom end for enabling said collection cup to be fixed against rotational movement when placed in said apparatus.

18. A subassembly adapted to be engaged with a test sample container for use in an apparatus for purifying and concentrating DNA, said subassembly comprising:
a gel matrix; and a retainer member for retaining the gel matrix, including means for enabling said retainer member to be disposed in said test sample container, said retainer member including at least three hoops, the gel matrix being confined between screens held by respective pairs of hoops, one of said hoops being common to said pairs;
and in which a first of said hoops comprises an axially extending ring at its inner periphery and a flange extending radially therefrom, a groove formed at the underside of said flange; said common hoop having a flange adapted to be fitted in said groove such that one of said pair of screens is held in said groove and extends across an opening defined by said inner ring.

* * * * *

UNITED STATES PATENT AND TRADEMARK OFFICE
CERTIFICATE OF CORRECTION

PATENT NO. : 4,863,582
DATED : Sep. 5, 1989
INVENTOR(S) : Antonio Wijangco, Theresa Guarino, Robert Zahensky It is certified that error appears in the above-identified patent and that said Letters Patent is hereby corrected as shown below:

Column 2, line 10, delete "collecting" and substitute --controlling--.
Column 5, line 3, delete "fill" and substitute --fit--.
Column 7, line 44, change "opn" to read --open--.
Column 7, line 51, delete "exist" and substitute --exit--.

Signed and Sealed this

Sixteenth Day of October, 1990

Attest:

HARRY F. MANBECK, JR.

*Attesting Officer*     Commissioner of Patents and Trademarks